United States Patent [19]
Stepniewski et al.

[11] Patent Number: 6,027,738
[45] Date of Patent: Feb. 22, 2000

[54] ANHYDROUS MATTE COSMETIC

[75] Inventors: George J. Stepniewski, Melville; David Peters, Amityville; Cecilia D. Benedicto, Plainview, all of N.Y.

[73] Assignee: E-L Management Corp., New York, N.Y.

[21] Appl. No.: 08/962,097

[22] Filed: Oct. 31, 1997

[51] Int. Cl.[7] .............................. A61K 6/00; A61K 7/00; A61K 7/025; A61K 31/74
[52] U.S. Cl. ............................. 424/401; 424/63; 424/64; 424/78.02
[58] Field of Search .................................. 424/78.02, 61, 424/401; 514/844, 845

[56] References Cited

U.S. PATENT DOCUMENTS

| | | | |
|---|---|---|---|
| 4,742,142 | 5/1988 | Shimizu et al. | 528/15 |
| 4,980,167 | 12/1990 | Harashima et al. | 424/401 |
| 5,043,155 | 8/1991 | Puchalski et al. | 424/78 |
| 5,252,761 | 10/1993 | Hirose et al. | 554/77 |
| 5,266,321 | 11/1993 | Shukuzaki et al. | 424/401 |
| 5,599,533 | 2/1997 | Stepniewski et al. | 424/78.02 |
| 5,648,066 | 7/1997 | Stepniewski | 424/64 |

FOREIGN PATENT DOCUMENTS 0 790 055 A1   8/1997   European Pat. Off. .

*Primary Examiner*—Thurman K. Page
*Assistant Examiner*—Sharon Howard
*Attorney, Agent, or Firm*—Dorene M. Price, Esq.; Karen A. Lowney, Esq.

[57] ABSTRACT

The present invention relates to an anhydrous makeup composition for topical application to the skin, the composition comprising (a) a silicone gel, the gel comprising an organopolysiloxane elastomer dispersed in a silicone-compatible vehicle, (b) and a silicone-oil base. The compositions of the invention produce a matte or non-shiny appearance when applied to the skin.

28 Claims, No Drawings

ANHYDROUS MATTE COSMETIC

FIELD OF THE INVENTION

The invention relates to makeup compositions. More specifically, the invention relates to silicone-based makeup compositions having a matte appearance.

BACKGROUND OF THE INVENTION

In recent years, there has been a strong trend toward the use of silicone fluids in makeup compositions. A major reason for their popularity is the elegant feel provided by the silicones: the product containing them goes onto the skin smoothly, with an excellent slip, and yet does not produce the greasy, heavy feel that non-silicone oils frequently leave. Silicone oils are now common components of virtually all types of makeup compositions, both liquid and powder, for example, foundations, concealers, eyeshadows and eyeliners, lipsticks and lip pencils, and blushes.

Another attractive aspect of the silicone oils is their tendency to produce a very shiny appearance on the skin to which they are applied. This is often desirable for certain types of cosmetics, particularly for those aimed at a younger consumer, to whom a glowing or glossy appearance is very appealing, or for cosmetics intended for evening wear, where subdued lighting permits a greater latitude in the shine produced by the cosmetic.

However, for certain types of cosmetic products, and/or for certain tyes of consumers, a significant amount of shininess is not desired and may even be inappropriate. A more mature user may not be flattered by a very glossy or shiny makeup. The fine lines and wrinkles which characterize a more mature skin are emphasized by a glossy product which ends to directly reflect light. More preferable for the consumer of a certain age is a makeup which will scatter or diffuse light, thereby providing a "soft focus", which blurs lines and hides blemishes. Attempts to achieve this type of masking in the past have largely relied on the use of higher levels of pigment, but this frequently results in a heavy, cakey product which does not flatter a majority of consumers.

Similarly, it may also simply be desirable to eliminate shininess for products to be used in certain environments. For example, glossy makeup is often perceived as inappropriate in a conservative office environment, and/or may be too glaring under the harsh lights of the typical office. In these circumstances, a more matte finish to the cosmetic product may be called for. Traditionally, this has been achieved by the addition of solid powders, such as mica, silica, talc, and the like, to the formulation. In the case of a silicone oil-based composition, however, counteracting the shine produced tends to be more difficult than with more traditional cosmetic oils, thus requiring addition of even greater amounts of the solid fillers. A larger proportion of solids in a formulation, however, results in a heavy, draggy feel on the skin, thereby canceling out to some extent some of the benefit of the silicone oils. Alternately, a more matte appearance can be achieved by including one or more volatile components, such as water or volatile oils, in the formulation; when the volatile evaporates upon application, this increases the concentration of pigment relative to the composition as a whole, resulting in a more matte look. However, this can also result in a dry, cakey look on the skin. Moreover, the use of volatiles, particularly water, is not appropriate and/or feasible in all products, such as anhydrous lipstick products, and also results in the necessity of finding specialized, and often expensive, airtight packaging to prevent loss of the volatile from the product in the package.

There is therefore a need for silicone oil-based formulations which do not confer a shiny or glossy appearance on the skin of the user, and which diffuse light, thereby reducing or minimizing the appearance of lines and wrinkles. There is also a need for a means for conferring a matte appearance to silicone oil-based compositions without the necessity for using a large proportion of solids in the formulation. The present invention provides such a method, as well as silicone oil-based formulations which retain the elegant feel of a silicone oil-based product while achieving a soft, non-shiny, or matte, appearance on the skin.

SUMMARY OF THE INVENTION

The invention relates to anhydrous silicone oil-containing makeup compositions for topical application to the skin, the compositions containing a silicone gel, the gel comprising an organopolysiloxane elastomer and a silicone-compatible oil vehicle. Preferably, the elastomer is a reaction product of an organopolysiloxane having an unsaturated group bound to a terminal Si-atom and an organohydrogensiloxane, which reaction product is at least partially cured.

It has been unexpectedly discovered that the addition of the aforementioned gels to an otherwise standard anhydrous silicone oil-based makeup formulation will effectively decrease the shiny appearance conferred by the presence of oils, particularly silicone oils. The resulting makeup compositions appear soft, light, and attractive on the skin, and diminish the appearance of lines and wrinkles of the user; the addition of the gel composition to a silicone oil-based anhydrous product also provides a matte finish on the skin without the addition of large quantities of solid fillers. Both these unexpected results are obtained while still retaining the desirable feel and slip of a silicone-based product.

DETAILED DESCRIPTION OF THE INVENTION

The gels employed in the present invention comprise a vehicle in which an organopolysiloxane elastomer is dispersed. The vehicle can comprise any cosmetically acceptable oil which is silicone-compatible. This vehicle can contain a silicone compatible ester, for example, the branched monoesters disclosed in U.S. Pat. No. 5,252,761, the contents of which are incorporated herein by reference. Such esters include, but are not limited to isooctyl isononanoate, isononyl isomyristate and isodecyl isononanoate. Other silicone compatible esters are isopropyl palmitate, isopropyl myristate, myristyl propionate, and cetyl octanoate.

More preferably, however, the vehicle comprises a silicone oil, car a combination of silicone oils, or a combination of a silicone oil with one of the aforementioned silicone-compatible esters. The silicone oil may be any volatile or non-volatile silicone oil, for example, any methylated linear or cyclic non-elastomeric organopolysiloxane, or combinations thereof. Preferably, however, the vehicle is a low-volatile silicone oil, such as dimethicone, phenytrimethicone, any organomodified dimethicone or trimethicone, or a mixture of such oils. In one embodiment, a preferred silicone oil is a low viscosity, low-volatile slicone, for example, a 20 cs dimethicone.

The gel is prepared by dispersing in the vehicle an organopolysiloxane elastomer. An elastomer is generally a chain polymer having a degree of cross-linking sufficient to provide a rubber-like material. In the present gel, the elastomer is an at least partially crosslinked or at least partially cured hetero-chain elastomer. Particularly preferred are those which are at least partially cured addition reaction products, i.e., hydrosilation products, or addition polymerization products, of an organopolysiloxane having unsaturated groups, such as vinyl or allyl, preferably bonded to at least one terminal silicon atom, and another silicone compound capable of participation in the addition reaction, such as an organohydrogenpolysiloxane. Suitable organopolysiloxane elastomers, having a three-dimensional cross-linked structure, are described, for example, in U.S. Pat. No. 5,266,321, the contents of which are incorporated herein by reference. However, other suitable elastomer materials are disclosed in, for example, U.S. Pat. Nos. 4,980,167 and 4,742,142.

A preferred organopolysiloxane is one which is at least partially crosslinked, or is an at least partially cured heterochain elastomer. In one preferred embodiment, the organopolysiloxane elastomer is one which is an at least partially cured addition reaction products, i.e., hydrosilation products, or addition polymerization products, of an organopolysiloxane having unsaturated groups, such as vinyl or allyl, preferably bonded to at least one terminal Si atom, and another silicon compound capable of participation in the addition reaction, such as an organohydrogen polysiloxane. A particularly preferred elastomer is polysilicone 11.

The chosen elastomer is dispersed in the vehicle by known homogenization techniques. The elastomer dispersed in the vehicle provides a soft, stable viscous gel, or gel-like material. Alternatively, the gel can be purchased premade, with the elastomer already dispersed in the vehicle. Such products are available under the name Gransil, for example Gransil DMG or Gransil PM, from Grant industries, Inc., Elmwood Park, N.J. The amounts of elastomer and vehicle may vary, depending on the desired viscosity, but generally should be in the range of 5–60%, elastomer and 40–95% vehicle.

Gels of this type have been previously disclosed for use in water-in-oil emulsion products, for example in U.S. Pat. No. 5,599,533. Silicone gels have also been reported in anhydrous non-silicone oil-based products in U.S. Pat. No. 5,266,321. However, they have not previously been used in anhydrous makeup products with a silicone-oil base, and the ability to reduce the shiny appearance of such products has not previously been disclosed. The addition of the gels in an anhydrous silicone-oil based makeup product yields a "soft-focus" type product, which on the skin blurs the hard lines and wrinkles common in older skin. The gels also permit the production of matte-finish products without the use of excessive amounts of solids.

The benefit of the addition of the gels can be obtained in any type of anhydrous silicone oil-based makeup composition, for example, foundations, eyeshadows, eyeliner, mascara, blushes, powders, lipsticks and lipglosses. In formulating the product, the silicone gel is simply added to a cosmetically acceptable anhydrous silicone-oil containing base. Alternately, the elastomer component of the gel can be added directly to the silicone-oil base.

By "silicone-oil base" in the present specification and claims is meant any anhydrous cosmetic base which contains sufficient silicone oil to yield a total silicone oil concentration in the composition as whole of least about 5% by weight, preferably at least about 10% by weight, more preferably at least about 20% of a silicone oil, up to an amount of about 80% by weight of the total composition, and most preferably in the range of about 20–60%. The silicone oil component of the base can be any volatile or non-volatile silicone, or any combination thereof. Suitable volatile oils include cyclic and linear silicones, such as hexamethylcyclotrisiloxane, octamethylcyclotetrasiloxane, and decamethylcyclopentasiloxane or volatile linear dimethylpolysioxanes; suitable non-volatile silicones include but are not limited to dimethicone, dimethiconol, phenyl trimethicone, simethicone, organomodified versions of any of these, or mixtures thereof. The oil component may also be a silicone surfactant, for example, a polyoxyalkylene modified organopolysiloxane, such as dimethicone coplyol.

The anhydrous silicone-oil base may be composed entirely of silicone oil. However, it will frequently be desirable to incorporate other non-silicone components. For example, the base may contain cosmetically acceptable non-silicone oils. Examples of suitable oils or oil-like emollients, as well as other optional ingredients, can be found in the International Cosmetic Ingredient Handbook, CTFA, 1996, the contents of which are incorporated herein by reference. Useful materials include, but are not limited to, castor oil coconut oil, corn oil, jojoba oil, cottonseed oil soybean oil, walnut oil, wheat germ oil, sunflower seed oil, palm kernel oil, calendula oil, C10–18 triglycerides, lanolin and lanolin derivatives, illipe butter, shea butter; straight or branched chain volatile hydrocarbons having from 8–20 carbon atoms, such as decane, dodecane, trid,cane, tetradecane, and C8–20 isoparaffins; nonvolatile hydrocarbons, such as isoparaffins, squalane, or petrolatum; esters having the formula RCO-OR' wherein RCO represents a cirboxylic acid radical and OR' represents an alcohol residue, such as isodecyl neopentanoate, tridecyl octanoate, cetil palmitate, cetyl octanoate, cetyl stearate, cetyl myristate, isopropyl palmitate, isopropyl myristate, polyglyceryl-2isostearate, neopentyl glycol distearate, isodecyl oleate, decyl isostearate, diisopropyl sebacate, PEG-4 diheptanoate, dioctyl malate, and isohexyl neopentanoate; and fatty alcohols, such as lanolin alcohol or oleyl alcohol.

It may al,so be desirable to incorporate one or more waxes in the composition, particularly if the product is a lipstick or other stick product. The term "wax" will be understood to encompass not only waxes in the traditional sense, i.e., those plant, animal or mineral waxes containing primarily esters of higher fatty acids and alcohols, free higher acids and alcohols, and saturated hydrocarbons, but also synthetic resinous products having a wax-like, i.e., hard, brittle, relatively non-greasy texture at room temperature, such as silicone waxes. Examples of suitable waxes include, but are not limited to, carnauba wax, candelilla wax, beeswax, microcrystalline wax, polyethylene, japan wax, synthetic wax, shellac wax, spermaceti, lanolin wax, ozokerite, bran wax, ceresin wax, bayberry wax, paraffin, rice wax, mink wax, montan wax, ouricoury wax, jojoba wax, and the like.

The amount and identity of the components of the anhydrous base will vary depending upon the nature and desired consistency and feel of the product to be made, and appropriate selection is within the routine skill in the art of cosmetic formulation. Generally, the oil and/or wax components of the anhydrous base will constitute from about 10 to about 80% of the composition as a whole. Particularly preferred, however, are non-volatile silicones, such as dimethicones having a viscosity of greater than 10 centistokes, alkylated dimethicones, such as cetyl or stearyl dimethicone, and trimethicones, such as phenyl trimethicone, in an amount of from about 10 to about 80%. A particular advantage is obtained when the oils used in the base are all or primarily non-volatile. It is relatively simple to produce a matte, or non-shiny, appearance when a significant quantity of the base comprises a volatile solvent: the volatiles simply evaporate off, leaving behind a high pigment concentration and a somewhat duller finish. However, as already noted above, the use of volatile solvents can be problematical and very costly. While the use of a non-volatile base is more practical, achieving a matte or non-shiny appearance is much more difficult. Thus, the present invention now makes it possible to obtain the desired non-shiny appearance even when the base is primarily or completely non-volatile.

Additional preferred components of the cosmetic compositions of the invention include one or more pigments. Any cosmetically acceptable pigment, either organic, inorganic, or combinations thereof, can be used in the makeup compositions of the invention. Examples of useful inorganic pigments include iron oxides (yellow, red, brown or black), ultramarines, chromium hydroxide green, chromium oxide, titanium dioxide(white), ferric ferrocyanide, ferric ammonium ferrocyanide, and mixtures thereof.

The organic pigments include natural colorants and synthetic monomeric and polymeric colorants. Exemplary are aromatic compounds such as azo, triphenylmethane, indigo, anthraquinone, and xanthine dyes, which are referred to as D&C or FD&C pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof. Pigment concentrations will vary depending upon the color of the final product, but generally will be in the range of from about 0.1–30% by weight of the total composition.

Another optional component of the formulation is one or more film-forming agents. The use of a film-former improves the wear of th? composition, and can confer transferresistance to the makeup product. Examples of useful film-forming agents include natural waxes, polymers such as polyethylene polymers and copolymers of PVP, dimethicone gum, and resin, such as shellac, polyterpenes, and various silicone resin,. A particularly preferred film-former is trimethylsiloxysilicate, used in an amount of from about 0.1–20%.

The composition can also contain small amounts of fillers or powders. Examples of such silica, talc, mica, starch, nylon, kaolin, bismuth oxychloride, or coated versions of each of these, for example, with lecithin, silicones, amino acids, fatty acids, fatty alcohols, or metallic soap coatings.

The composition can also contain other optional components including, but not limited to, oil soluble sunscreens, such as Octyl Methoxycinnamate; particulate sunscreens such as Zinc Oxide; oil-soluble antioxidants and/or preservatives, such as BHT; chelating agents such as Disodium EDTA; fragrances (such as pinene); flavoring agents; waterproofing agents (such as PVP/Eicosene Copolymer); surfactants, such as silicone copolyols or fatty acid glycerol esters; and oil-soluble actives, such as tocopherol and its derivatives or retinol and its derivatives; and the like.

In one preferred embodiment, the makeup product of the invention is a solid silicone stick, particularly a lipstick. Particularly preferred is solid silicone compositions comprising a low molecular weight polyethylene as a gelling agent for the silicone base. Such compositions are described in detail in U.S. Pat. No. 5,648,066, the contents of which are incorporated herein by reference. Briefly, a straight-chain homopolymer of polyethylene having an average molecular weight of about 500 or less is employed as a solidifying agent for a non-volatile silicone fluid, such as dimethicone or phenyl trimethicone, or combinations thereof. Preferably, the silicone composition contains from about 3 to about 20% polyethylene by weight of the composition, and from about 20 to about 95% of non-volatile silicone fluid. When this combination is used as a base, the silicone gel is added thereto in an amount of from about 1–50% by weight of the entire composition.

The invention is further illustrated by the following non-limiting example.

EXAMPLES

I. Lipstick Formulation

| Material | Weight % |
|---|---|
| Polysilicone 11 | 5.0 |
| (50% organopolysiloxane elastomer in dimethicone) | |
| Dimethicone/trimethylsiloxysilicate | 2.0 |
| (32% trimethylsiloxysilicate) | |
| Dimethicone | 4.0 |
| Stearyl dimethicone | 1.0 |
| Phenyl trimethicone | 39.0 |
| Squalane | 5.0 |
| Jojoba oil | 5.0 |
| Mica | 8.0 |
| Dimethicone | 8.0 |
| Polyethylene | 8.5 |
| Silica | 2.5 |
| Titanium dioxide | 0.8 |
| Iron oxides | 0.1 |
| D&C Red No. 6 | 1.0 |
| Iron oxides | 1.1 |
| D&C Red No. 7 calcium lake | 9.0 |

The pigments of the above formula are ground with appropriate equipment in a portion of the oil component. In a separate kettle, all the remaining components are heated to 90–95° C., with a agitation. To this mixture is added the predispersed gel under agitation until homogeneous. The pigments are added, the mixture cooled to pouring temperature, about 90° C., and poured into an appropriate mold.

II. Measurement of Matte Appearance

The matte appearance conferred by the formulations of the invention is evaluated by comparing two otherwise identical lipstick formulations, one containing 10; of a silicone gel and the other without. Both lipsticks are smeared onto Leneta Color Matching Applicator Cards. Gloss readings are then taken using a 60 degree Gardner Gloss Meter to demonstrate a reduction in the glossy appearance of the lipstick of the invention. The higher the number of gloss units, the higher the gloss of the lipstick. A difference of 10 gloss units indicates a visually distinctive difference in gloss.

The results show the lipstick with no silicone gel measuring 57 gloss units, and the lipstick with silicone gel measuring 36 closs units, clearly showing a significant decrease in the shiny appearance of the lipstick of the invention.

What we claim is:

1. An anhydrous makeup composition for topical application to the skin, the composition comprising (a) a silicone gel, the gel comprising an organopolysiloxane elastomer dispersed in a silicone-compatible vehicle, (b) and a silicone-oil base.

2. The composition of claim 1 in which the silicone-compatible vehicle is an ester or a silicone oil.

3. The composition of claim 2 in which the silicone oil is a dimethicone, an alkyl dimethicone, a trimethicone, or a combination thereof.

4. The composition of claim 1 which further comprises one or more pigments.

5. The composition of claim 1 which comprises at least about 10% by weight of the total composition of a silicone oil in the silicone-oil base.

6. The composition of claim 5 in which the silicone oil in the silicone-oil base is a non-volatile silicone oil.

7. The composition of claim 5 in which the silicone oil is a dimethicone, an alkyl dimethicone, a trimethicone, or a combination thereof.

8. The composition of claim 1 which has a matte appearance when applied to the skin.

9. The composition of claim 1 which is a lipstick.

10. The composition of claim 1 which is a foundation.

11. A anhydrous makeup composition for topical application to the skin, the composition comprising (a) a silicone gel, the gel comprising an organopolysiloxane elastomer dispersed in a silicone oil vehicle, (b) and a silicone-oil base, the composition as a whole comprising at least about 10% by weight of a silicone oil.

12. The composition of claim 11 which comprises at least about 20% by weight of a silicone oil.

13. The composition of claim 11, which comprises at least about 20% of a non-volatile silicone oil.

14. The composition of claim 11 which comprises at least about 20% of one or more of a non-volatile silicone oil selected from the group consisting of a dimethicone, an alkyl dimethicone, and a trimethicone.

15. The composition of claim 11 which also comprises one or more pigments.

16. The composition of claim 11 which also comprises a film forming agent.

17. The composition of claim 11 which comprises (a) a gel comprising an organopolysiloxane elastomer dispersed in a dimethicone vehicle, and (b) a non-volatile silicone oil base, wherein the composition comprises at least about 30% of a non-volatile silicone oil.

18. The composition of claim 17 which comprises at least about 30% of one or more of the silicone oils selected from the group consisting of dimethicone, an alkyl dimethicone, and a trimethicone.

19. The composition of claim 17 which comprises one or more pigments in an amount of from about 0.1–30%.

20. The composition of claim 19 which also comprises a film forming agent in an amount of from about 0.1–20%.

21. The composition of claim 20 in which the film forming agent is trimethylsiloxysilicate.

22. The composition of claim 11 which is a lipstick or a foundation.

23. The composition of claim 20 which is a lipstick or a foundation.

24. A method of increasing the matte appearance of a cosmetic composition which comprises adding to the composition an amount of a silicone gel effective to increase the matte appearance of the composition, the gel comprising an organopolysiloxane elastomer and a silicone compatible vehicle.

25. An anhydrous matte lipstick composition comprising (a) a silicone gel, the gel comprising an organopolysiloxane elastomer dispersed in a silicone oil vehicle; (b) a silicone oil base comprising a nonvolatile silicone oil; and (c) a straight-chain homopolymer polyethylene having an average molecular weight of about 500 or less.

26. The lipstick of claim 25 which also comprises a film forming agent.

27. The lipstick of claim 26 in which the film forming agent is trimethylsiloxysilicate.

28. The composition of claim 25 which also comprises one or more pigments.

* * * * *